US009131951B2

(12) United States Patent
Mirza et al.

(10) Patent No.: US 9,131,951 B2
(45) Date of Patent: Sep. 15, 2015

(54) ENDOSCOPIC SURGICAL BLADE AND METHOD OF USE THEREOF

(71) Applicant: A.M. SURGICAL, INC., Smithtown, NY (US)

(72) Inventors: Ather Mirza, Smithtown, NY (US); Romi Mirza, Smithtown, NY (US)

(73) Assignee: A.M. SURGICAL, INC., Smithtown, NY (US)

( * ) Notice: Subject to any disclaimer, the term of this patent is extended or adjusted under 35 U.S.C. 154(b) by 230 days.

(21) Appl. No.: 13/963,722

(22) Filed: Aug. 9, 2013

(65) Prior Publication Data

US 2014/0012076 A1 Jan. 9, 2014

Related U.S. Application Data

(63) Continuation of application No. 13/410,392, filed on Mar. 2, 2012, now Pat. No. 9,028,504.

(51) Int. Cl.
*A61B 17/32* (2006.01)
*A61B 1/012* (2006.01)
*A61B 1/04* (2006.01)

(52) U.S. Cl.
CPC ......... *A61B 17/320016* (2013.01); *A61B 1/012* (2013.01); *A61B 1/04* (2013.01); *A61B 17/320036* (2013.01)

(58) Field of Classification Search
CPC ............... A61B 17/320036; A61B 17/3213; A61B 17/3211; A61B 17/320016; A61B 17/1686; A61B 2017/320052; A61B 2017/32113; A61F 9/0133

USPC .................. 606/167, 170; 600/104
See application file for complete search history.

(56) References Cited

U.S. PATENT DOCUMENTS

| 5,282,816 | A | * | 2/1994 | Miller et al. | 606/167 |
|---|---|---|---|---|---|
| 5,366,465 | A | * | 11/1994 | Mirza | 606/170 |
| 5,649,946 | A | * | 7/1997 | Bramlet | 606/167 |
| 6,685,717 | B1 | * | 2/2004 | Ilic | 606/167 |
| 2007/0112366 | A1 | | 5/2007 | Welborn et al. | |
| 2007/0233163 | A1 | | 10/2007 | Bombard et al. | |
| 2007/0288043 | A1 | * | 12/2007 | Rehnke | 606/170 |
| 2010/0069936 | A1 | * | 3/2010 | Palmer et al. | 606/167 |
| 2010/0228083 | A1 | | 9/2010 | Mirza et al. | |
| 2011/0130779 | A1 | | 6/2011 | Mirza et al. | |

OTHER PUBLICATIONS

International Search Report and Written Opinion issued in International Patent Application No. PCT/US2012/027456 mailed Oct. 24, 2012.
File history of U.S. Appl. No. 13/410,392, filed Mar. 2, 2012.

* cited by examiner

*Primary Examiner* — Katherine M Shi
(74) *Attorney, Agent, or Firm* — Ping Wang; Andrews Kurth LLP

(57) ABSTRACT

An endoscopic surgical blade is disclosed. The blade is of a low-profile design, having a downward angled cutting surface that is radiused at its upper end. The blade is part of an endoscopic knife assembly which also contains a knife tube. The endoscopic knife assembly is for use in endoscopic surgery by insertion of the assembly through a slotted cannula. The knife tube is hollow and allows the insertion of an endoscope for viewing of the surgical procedure. A method for a performing an operative procedure on a target tissue in a subject using an endoscopic knife assembly having a low-profile, downward angled blade is also described.

16 Claims, 11 Drawing Sheets

ENDOSCOPIC SURGICAL BLADE AND METHOD OF USE THEREOF

This application is a continuation application of U.S. patent application Ser. No. 13/410,392, filed Mar. 2, 2012. The entirety of the aforementioned application is incorporated herein by reference.

FIELD

This application generally relates to medical devices. In particular, the application relates to devices and methods for endoscopic surgery, e.g., for endoscopic trigger release surgery.

BACKGROUND

Endoscopic surgery is a minimally invasive surgical procedure that is performed through small incisions or natural body openings. An endoscopic procedure typically involves use of specialized devices and remote-control manipulation of instruments with indirect observation of the surgical field through an endoscope or similar device. Comparing to open surgery, endoscopic surgery may result in shorter hospital stays, or allow outpatient treatment.

Trigger finger is characterized by catching, snapping or locking of the involved finger flexor tendon, associated with dysfunction and pain. Localized inflammation or nodular swelling of said flexor tendon causes a disparity in size between the flexor tendon and the surrounding retinacular pulley system, most commonly at the level of the first annular (A1) pulley. When the subject extends the involved finger, the tendon will "catch" on the pulley, followed by an abrupt popping of the tendon through the pulley. This results in a difficulty flexing or extending the finger and the "triggering" phenomenon.

Typically, a first course of treatment for trigger finger is corticosteroid injections into the tendon sheath to reduce inflammation. When corticosteroid injection is not or no longer effective, surgical division of the A1 pulley is indicated. Conventional surgical techniques for trigger finger release require a fairly large incision over the A1 pulley and spreading of the incision to allow viewing and instrument access. These techniques can require a longer period of recovery than endoscopic methods and have greater levels of post-operative pain due to the incision size and level of manipulation during the procedure. Previous endoscopic techniques for trigger finger release require two incisions, one proximal and one distal to the A1 pulley and the threading of a cannula through the two incisions. An arthroscope is then inserted in the distal end of the cannula, while a cutting tool is inserted in the proximal opening. The cutting tool and arthroscope are then alternately moved forward or backward through the cannula. This does not allow direct visualization of the procedure from the point of view of the cutting tool during the separation of the pulley. Accordingly, the present application fulfils a need in the art for a minimally invasive surgical procedure for the treatment of trigger finger by providing a method for uniportal endoscopic trigger release surgery and a low-profile endoscopic surgical blade with a downward angled blade.

SUMMARY

One aspect of the present application relates to a low-profile blade for an endoscopic knife assembly, comprising a cutting surface at its distal end that is angled downward and having a non-cutting radiused surface at the top end of the cutting surface, wherein the blade is sized to fit at a tip of an endoscope.

Another aspect of the present application relates to an endoscopic knife assembly, comprising: a knife tube having a distal end and a proximate end and a low-profile blade that has a downward angled cutting surface that is radiused at its upper end attached to the distal end.

Another aspect of the present application relates to an instrument kit for implementing an endoscopic surgical procedure comprising: an endoscopic knife assembly comprising a low-profile blade that has a downward angled cutting surface that is radiused at its upper end and a knife tube.

Another aspect of the present application relates to a method for treating trigger finger, comprising: establishing an entry portal at a location proximal to the A1 pulley, inserting a cannula having open proximal and distal ends and an open slot extending along the length of the cannula, inserting an endoscope into the cannula, said endoscope comprising an endoscopic knife assembly having a low-profile blade that has a downward angled cutting surface that is radiused at its upper end, advancing said endoscope so that the blade moves in contact with the A1 pulley through the slot, operatively engaging the A1 pulley with the blade, and advancing the blade through the cannula to divide the A1 pulley.

BRIEF DESCRIPTION OF THE DRAWINGS

The present invention can be better understood by reference to the following drawings. The drawings are merely exemplary to illustrate certain features that may be used singularly or in combination with other features and the present invention should not be limited to the embodiments shown.

FIG. 1A depicts a side view of the blade component, showing the cutting surface, the transition where the blade is joined to a knife tube and the taper at the end of the blade. FIG. 1B is a cross section view of the blade at the bisecting line X-X in FIG. 1A depicting an exemplary angle of a cutting surface of the blade component. FIG. 1C is a perspective view of the blade from the back depicting the width of the blade and the transition. FIG. 1D depicts a side view of another embodiment of the blade component.

FIG. 2A depicts a side view of the blade component, showing the cutting surface, the transition where the blade is joined to a knife tube and the taper at the end of the blade. FIG. 2B is a cross section view of the blade at the bisecting line X-X in FIG. 2A depicting an exemplary angle of a cutting surface of the blade component. FIG. 2C is a perspective view of the blade from the back depicting the width of the blade and the transition.

FIG. 3A is a perspective view of the endoscopic knife assembly from above, without a locking nut. FIG. 3B is a perspective view of the endoscopic knife assembly from the side, including a locking nut. FIG. 3C is a cross section view of the endoscopic knife assembly and locking nut at the bisecting line Y-Y in FIG. 3B, as viewed in the direction of the arrows. FIG. 3D is a perspective view of the endoscopic knife assembly from the distal end. FIG. 3E is a perspective view of the endoscopic knife assembly from the proximate end.

FIG. 4A is a three-dimensional perspective view of a knife tube at an angle. FIG. 4B is a perspective view of the knife tube, showing the slots and a handle. FIG. 4C is a perspective view of the knife tube rotated 90 degrees from the view in FIG. 4B, showing the slots and a handle. FIG. 4D is a cross section view of the endoscopic knife tube and handle at the bisecting line Z-Z in FIG. 4C, as viewed in the direction of the arrows.

FIG. 5A is a perspective view of the endoscopic knife assembly from the side. FIG. 5B is a perspective view of the endoscopic knife assembly from the top. FIG. 5C is a perspective view of the endoscopic knife assembly from the bottom. FIG. 5D is a perspective view of the endoscopic knife assembly from the distal end.

FIG. 6A is a perspective view of the endoscopic knife assembly from the side. FIG. 6B is a perspective view of the endoscopic knife assembly from the top. FIG. 6C is a perspective view of the endoscopic knife assembly from the bottom. FIG. 6D is a perspective view of the endoscopic knife assembly from the distal end.

FIG. 8A is a perspective view at an angle as seen from the bottom, showing the flattened bottom face of the alignment ring. FIG. 8B is a perspective view at an angle as seen from the front or back face of the alignment ring. FIG. 8C is a perspective view seen from the side of the alignment ring. FIG. 8D is a perspective view seen from the top of the alignment ring.

DETAILED DESCRIPTION

Figure 1:
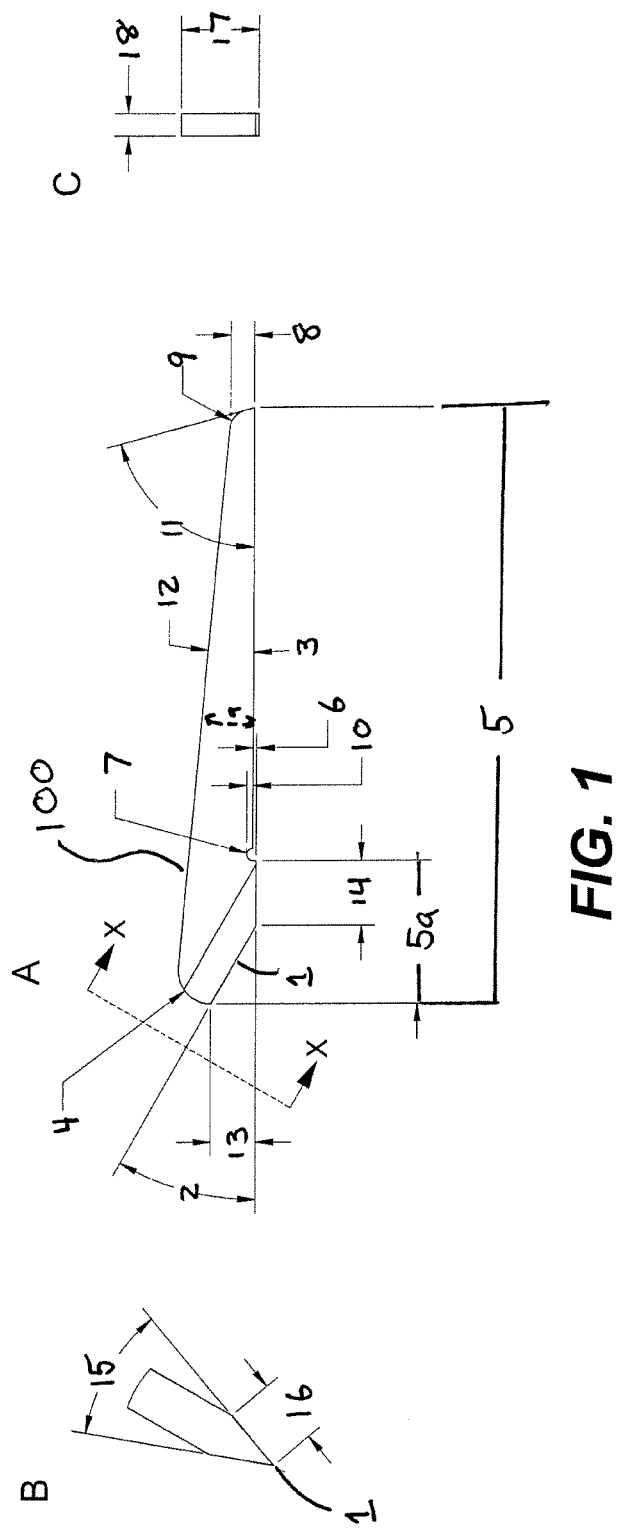
FIGS. 1A-D illustrate a blade component of an endoscopic knife assembly.
Figure 1:
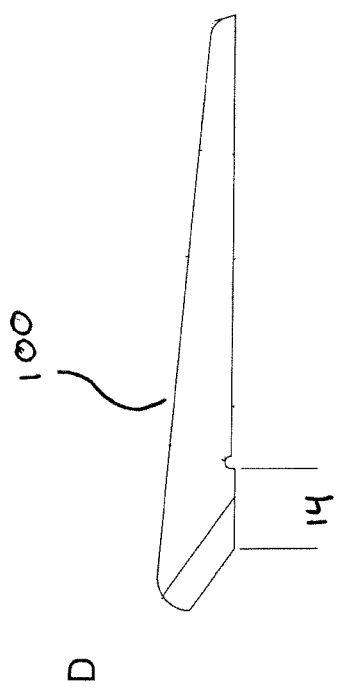

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention. Descriptions of specific applications are provided only as representative examples. The present invention is not intended to be limited to the embodiments shown, but is to be accorded the widest possible scope consistent with the principles and features disclosed herein.

The present application generally relates to endoscopic surgical device and method for endoscopic trigger release surgery.

This description is intended to be read in connection with the accompanying drawings, which are to be considered part of the entire written description of this application. The drawing figures are not necessarily to scale and certain features of the application may be shown exaggerated in scale or in somewhat schematic form in the interest of clarity and conciseness. In the description, relative terms such as "front," "back," "up," "down," "top," "bottom," "upper," "lower," "distal," and "proximate" as well as derivatives thereof, should be construed to refer to the orientation as then described or as shown in the drawing figure under discussion. These relative terms are for convenience of description and normally are not intended to require a particular orientation. Terms concerning attachments, coupling and the like, such as "connected," "mounted," and "attached," refer to a relationship wherein structures are secured or attached to one another either directly or indirectly through intervening structures, as well as both movable or rigid attachments or relationships, unless expressly described otherwise.

The term "trigger finger," as used herein, also refers to "trigger digit," "trigger thumb," and "stenosing tendovaginitis."

The blade described herein is a low-profile blade that has a downward angled cutting surface that is radiused at its upper end to prevent damage to the underlying tendon during the separation of the A1 pulley. This downward angle allows the blade described herein to maintain a low profile such that it can be used with a slotted cannula for the precise division of the A1 pulley.

The presently described low-profile blade is sized to fit at the tip of an endoscope and form a component of an endoscopic knife assembly, wherein the blade is welded onto a hollow knife tube that allows the practitioner to extend an endoscopic camera through the hollow knife tube to allow direct visualization of the tissue and blade before, during and after the cutting of the target tissue. Particular embodiments of the endoscopic knife assembly further comprise a handle at its proximal end that allows the direct manual manipulation of the endoscopic knife assembly. The handle also comprises a hollow lumen that allows an arthroscope to be passed through the handle into the knife tube, allowing direct visualization of the tissue and blade before, during and after the cutting of the target tissue. Other embodiments of the knife tube assembly comprise an alignment ring and slots at the proximate end to allow the knife tube assembly to be mated with the locking mechanism of an endoscopic surgical system.

One aspect of the present application relates to a low-profile blade for an endoscopic knife assembly, comprising a cutting surface at its distal end that is angled downward and having a non-cutting radiused surface at the top end of the cutting surface. As used herein, the term "low-profile" means that the body of the blade does not protrude more than 2.5 mm through the slot on a slotted cannula.

Figure 5:
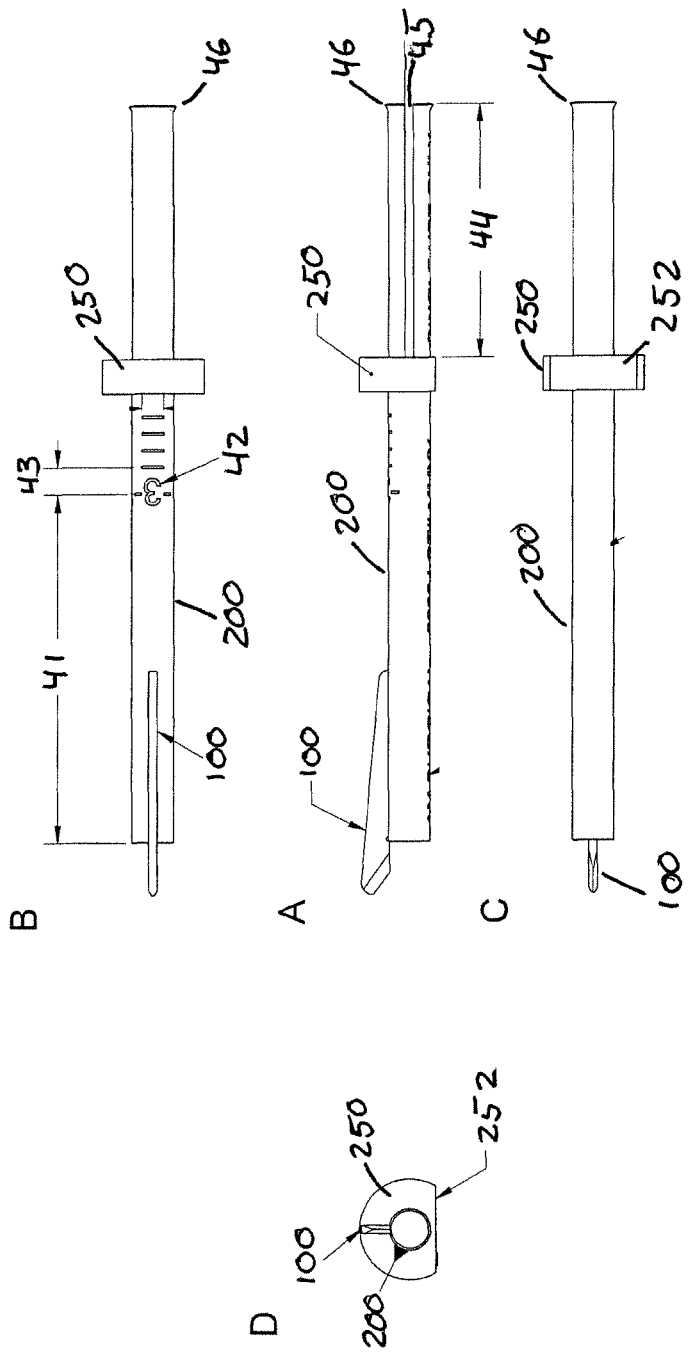
FIGS. 5A-D illustrate an endoscopic knife assembly.
Figure 6:
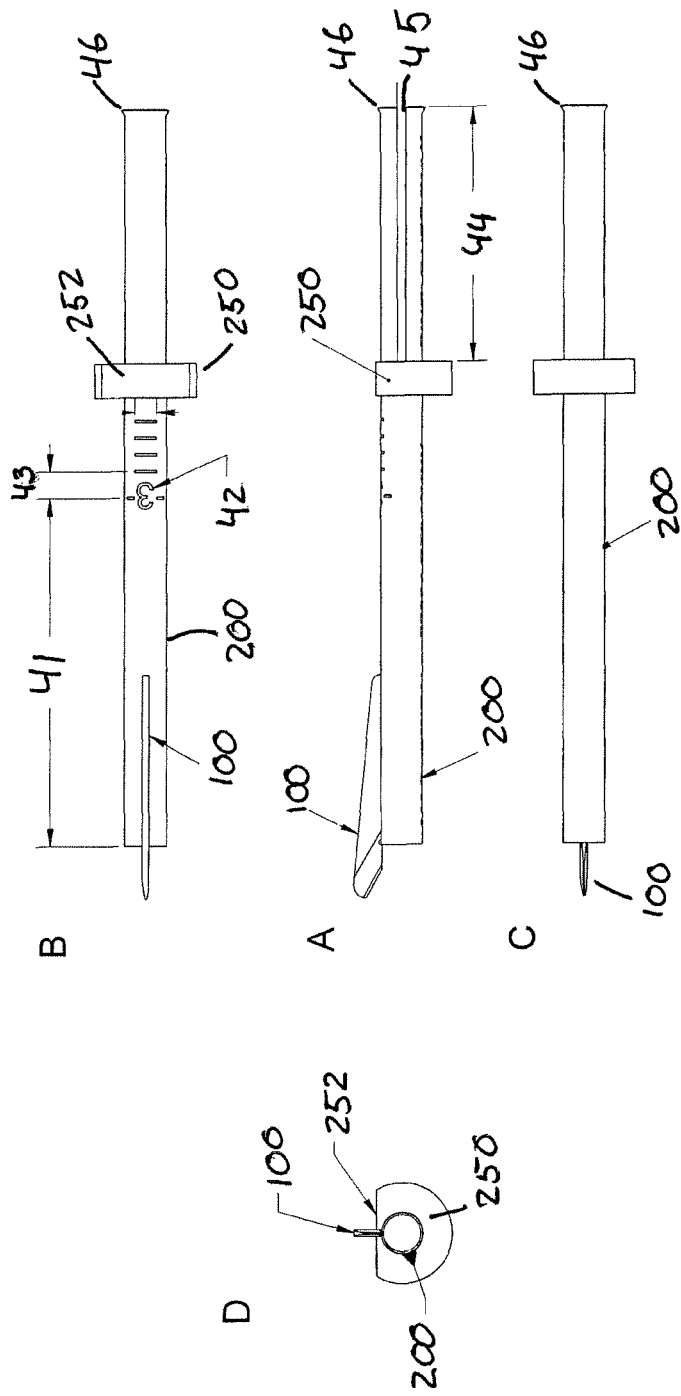
FIGS. 6A-D illustrate another embodiment of an endoscopic knife assembly.
Figure 7:
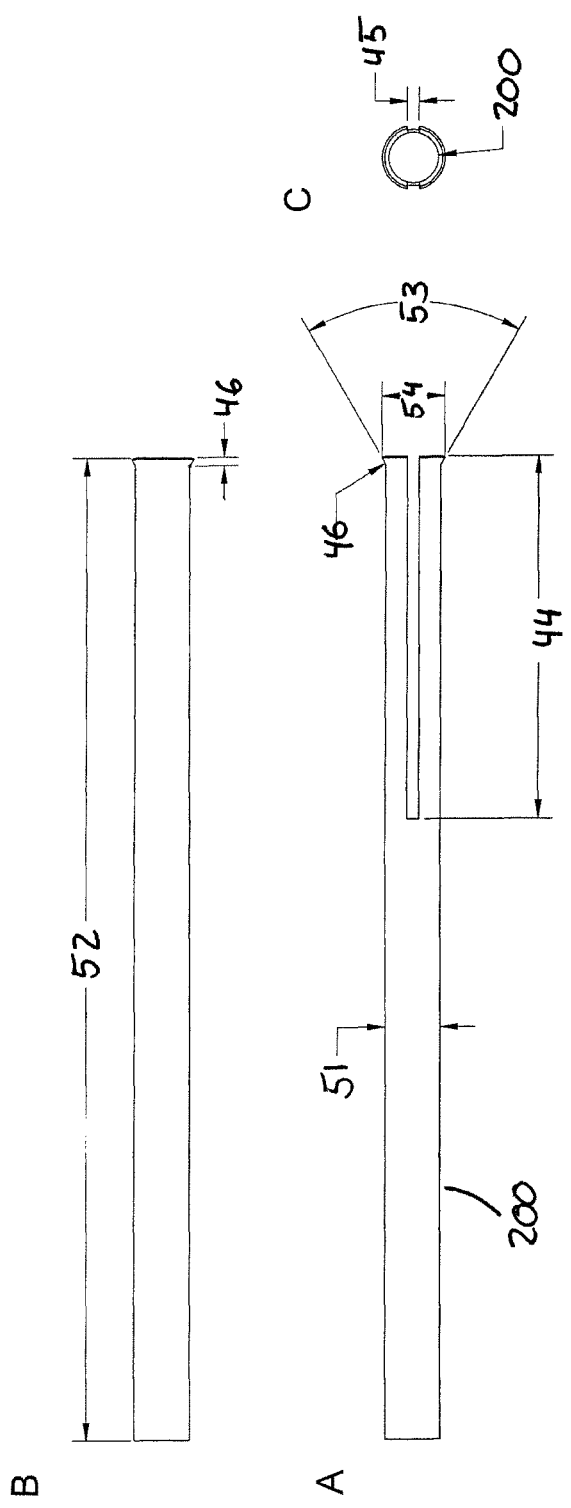
FIGS. 7A-C are perspective views of a knife tube without an affixed blade or alignment ring and without gradations.

In one particular embodiment, the downward angle of the cutting surface, which is defined as shown in FIGS. 5 and 6 is between about 25 degrees and about 50 degrees. In a more particular embodiment, the downward angle is between about 30 degrees and about 45 degrees. In a still more particularly embodiment, the downward angle is between about 30 degrees and about 40 degrees. In a further embodiment, the downward angle is about 36 degrees. In another further embodiment, the downward angle is about 30 degrees.

In one particular embodiment, the proximate section of the blade body has a tapered end.

In another particular embodiment, the blade body comprises a notch on the lower edge to engage with a knife tube.

In another particular embodiment, the blade has a total vertical height in the range of about 1.8 mm to about 2.6 mm.

Another aspect of the present application relates to an endoscopic knife assembly, comprising: a knife tube having a distal end and a proximate end and a low-profile blade that has a downward angled cutting surface that is radiused at its upper end attached to the distal end.

In a further embodiment, the endoscopic knife assembly further comprises a handle at the proximal end of the knife tube.

In a still further embodiment, the handle comprises compression fingers for gripping the knife tube and a threaded region for the attachment of a clamping nut.

In another still further embodiment, the handle is bonded to the knife tube. In a related embodiment the handle is bonded with epoxy.

In another further embodiment, the knife tube comprises an alignment ring attached near the proximate end and one or more slots at the proximate end for the attachment of a locking assembly to the knife tube and alignment ring.

In related embodiment, the slots are located on a plane that is perpendicular to the blade attached to the distal end of the knife tube.

In another related embodiment, the alignment ring comprises a flattened surface that is positioned perpendicular to the hook blade attached to the distal end of the knife tube.

In another particular embodiment, the knife tube is marked on the top or side surface with gradations.

In another particular embodiment, the blade is welded to the knife tube.

Another aspect of the present application relates to an instrument kit for implementing an endoscopic surgical procedure comprising: an endoscopic knife assembly comprising a low-profile blade that has a downward angled cutting surface that is radiused at its upper end and a knife tube.

In a further embodiment, the endoscopic knife assembly further comprises a handle at the proximal end of the knife tube.

In a still further embodiment, the handle comprises compression fingers for gripping the knife tube and a threaded region for the attachment of a clamping nut.

In another still further embodiment, the handle is bonded to the knife tube. In a related embodiment the handle is bonded with epoxy.

In another further embodiment, the knife tube comprises an alignment ring attached near the proximate end and one or more slots at the proximate end for the attachment of a locking assembly to the knife tube and alignment ring.

In another further embodiment, the kit further comprises a cannula having an open slot extending along the length of the cannula.

In another particular embodiment, the cannula is a clear cannula.

In another further embodiment, the kit further comprises an obturator.

In another further embodiment, the kit further comprises an elevator.

In another further embodiment, the kit further comprises an arthroscope.

Another aspect of the present application relates to a method for a performing an operative procedure on a target tissue in a subject, comprising: establishing an entry portal, inserting a cannula having open proximal and distal ends and an open slot extending along the length of the cannula, inserting an endoscope into the cannula, said endoscope comprising an endoscopic knife assembly having a low-profile blade that has a downward angled cutting surface that is radiused at its upper end, advancing said endoscope so that the blade moves in contact with the target tissue through the slot, operatively engaging the target tissue with the blade, and advancing the blade through the cannula to divide the target tissue.

In one particular embodiment, the operative procedure is trigger finger release.

In another particular embodiment, the establishing an entry portal comprises making an incision.

In another particular embodiment, the target tissue is the A1 pulley.

In another particular embodiment, the inserting of said endoscope comprising an endoscope comprising an endoscopic knife assembly having a low-profile blade that has a downward angled cutting surface that is radiused at its upper end is preceded by the insertion of another endoscope comprising a means for visualization of the target tissue.

In a particular embodiment, the cannula is a clear cannula.

In a further embodiment, the method further comprises visualization of anatomic structures surrounding the cannula.

One aspect of the present invention relates to a low-profile downward angled endoscopic surgical blade. The design of the present blade is such that it is usable in endoscopic surgery in a manner that allows the practitioner to extend the blade through the cannula to the target tissue without damage to surrounding tissue and/or organs. The blade is made from materials commonly used for surgical blades or scalpels, such materials include, but are not limited to, hardened and tempered steel, stainless steel, high carbon steel, titanium, alloys and ceramic.

In particular embodiments, the blade is made from stainless steel. In a further embodiment, the stainless steel is martensitic stainless steel. An exemplary martensitic stainless steel is Bohler-Uddeholm AEB-L martensitic stainless steel. In a still further embodiment, the martensitic stainless steel is heat-treated. In another further embodiment, the stainless steel is 440 A stainless steel. In a particular embodiment, the blade is made from Hitachi GIN-5 SST-MODIFIED 440-A stainless steel. The blade is optionally flash electropolished. The cutting edges are machine finished and must be sharp. In a particular embodiment, the steel of the blade is heat-treated to Rockwell C hardness of about 50-72. In a more particular embodiment, the steel of the blade is heat-treated to Rockwell C hardness of 58-64.

FIG. 1A depicts a side view of the blade component of the endoscopic knife assembly, showing the cutting surface at the leading end of the blade, the transition where the blade is joined to the knife tube and the taper at the trailing end of the blade.

FIG. 1B is an view depicting an exemplary angle of the cutting surface of the blade as viewed from the perspective of the line X-X in FIG. 1A.

FIG. 1C is a perspective view of the blade from the back depicting the width of the blade and the transition between the mounting surface and the lower end of the cutting surface below the transition.

FIG. 1D depicts a side view of another embodiment of the blade component.

In a particular embodiment, the blade 100 as shown in FIG. 1A comprises a cutting surface 1 on the leading end of the blade, which is at an angle 2 with respect to the horizontal orientation of the blade 100, as defined by the mounting surface 3 of the blade. The angle 2 is such that the top of cutting surface 1 is forward of the bottom of the cutting surface. In one embodiment the angle 2 is between about 30 and about 45 degrees. In a particular embodiment, the angle 2 is between about 33 and about 39 degrees. In a more particular embodiment, the angle 2 is about 36 degrees.

In some embodiments, the upper end 4 of the cutting surface 1 is radiused. The radiused upper end 4 of the cutting surface 1 is about 90 degrees of a circle and has a radius measurement between about 0.50 mm and 1.50 mm. In a particular embodiment, the radius is about 0.94 mm.

In some embodiments, the cutting surface 1 has a vertical height 13 between about 0.80 mm and about 1.70 mm. In particular embodiments, the vertical height 13 is between about 1.00 mm and 1.50 mm. In a more particular embodiment, the vertical height 13 is about 1.27 mm.

In a particular embodiment, the total length 5 of the blade from the leading point of the cutting surface 1 to the trailing end of the blade is between about 13 mm and about 21 mm.

In another particular embodiment, the total length 5 of the blade from the leading point of the cutting surface to the trailing end of the blade is between about 15 mm and about 19 mm. In a more particular embodiment the total length 5 of the blade is about 16.69+/−0.254 mm. In a particular embodiment, the length 5a of the forward section of the blade from the leading point of the cutting surface 1 to the leading edge of the notch 7 is between about 2 mm and about 8 mm. In another particular embodiment, the length 5a of the forward section of the blade from the leading point of the cutting surface to the leading edge of the notch 7 is between about 3 mm and about 5 mm. In a more particular embodiment the length 5a of the forward section of the blade is about 4+/−0.254 mm.

In order to insure that, during manufacture, the blade is consistently joined to the knife tube in the same location, the lower surface of the main body of the blade comprises a transition 6, the distal end of which meets the notch 7 in the lower surface of the main body of the blade. During assembly of the endoscopic knife assembly, the mounting surface 3 is aligned with and positioned on the forward end of the knife tube. Following the positioning of the blade on the knife tube, the blade is laser welded all around to the knife tube. In a particular embodiment, the strength of the weld is tested by applying torque to the unit, for example about 10 in-lbs of torque. In a first embodiment, the depth of the transition 6 is between about 0.03 mm and about 0.18 mm. In a particular embodiment, the depth of the transition 6 is between about 0.05 mm and about 0.15 mm. In a more particular embodiment, the depth of the transition 6 is about 0.10 mm.

In particular embodiments, the blade further comprises a notch 7 on the lower edge of the blade between the mounting surface 3 and the cutting surface 1. In particular embodiments, the notch 7 is relatively semi-circular in shape, having a radius of between about 0.1 mm and about 0.3 mm, more particularly about 0.18 mm. The top of the notch 7 is recessed 10 into the body of the blade, with respect to the bottom end of the cutting surface 1, between about 0.1 mm and about 0.3 mm, more particularly about 0.18 mm.

In particular embodiments, the horizontal distance 14 between the bottom of the leading edge of the cutting surface 1 and the notch 7 can be different, dependent upon the application for the blade. In some embodiments, the horizontal distance is between about 1.50 mm and about 2.50 mm. In a more particular embodiment, the horizontal distance 14 is about 1.80 mm, as exemplified in FIG. 1A. In another more particular embodiment, the horizontal distance 14 is about 2.26 mm, as exemplified in FIG. 1D.

In order to prevent the blade from catching on tissues or a cannula when the blade is drawn backwards through a cannula tube, the trailing edge 8 of the blade is angled down to the knife tube and the top of the trailing edge 8 is radiused 9. In a particular embodiment, the vertical height of the trailing edge 8 is between about 0.50 mm and about 0.88 mm, more particularly about 0.60 mm to about 0.70 mm. In a more particular embodiment, the vertical height of the trailing edge 8 is about 0.66 mm. In some embodiments, the radius 9 at the top of the trailing edge 8 is between about 0.40 mm and about 0.80 mm. In further embodiments, the radius 9 at the top of the trailing edge 8 is between about 0.50 mm and about 0.70 mm, more particularly about 0.61 mm.

In some embodiments the trailing edge 8 is canted forward at an angle 11 from the vertical with respect to the horizontal line of the mounting surface 3. in particular embodiments, the forward angle 11 of the trailing edge 8 is between about 30 degrees and about 90 degrees. In further embodiments, the angle 11 is between about 45 degrees and about 85 degrees. In more particular embodiments, the angle 11 is between about 65 degrees and about 80 degrees. In a most particular embodiment, the angle 11 is about 75 degrees.

In some embodiments, the top edge 12 of the blade 100 forms an angle 19 with respect to bottom edge 3, sloping downward as defined by FIG. 1A from where it meets the radius 4 at the top of cutting surface 1 to where it meets the radius 9 at the top of the trailing edge 8. In particular embodiments, the angle 19 of the top edge 12 is between about 2.5 degrees and about 10 degrees. In more particular embodiments, the angle 19 of the top edge 12 is between about 3.5 degrees and about 7 degrees. In a still more particular embodiment, the angle 19 of the top edge is about 5 degrees.

Referring now to FIG. 1B, the cutting surface 1 is a single beveled cutting surface and the angle 15 is between about 30 degrees and about 50 degrees. In some embodiments, the angle 15 is between about 35 degrees and about 45 degrees. In a particular embodiment, the angle 15 is about 40 degrees.

Referring to FIG. 1C, in a particular embodiment, the height 17 of the body of the blade is between about 1.8 mm and about 2.6 mm. In another embodiment, the height 17 of the body of the blade is between about 2.1 mm and about 2.3 mm. In a particular embodiment, the height 17 of the body of the blade is between about 2.15 mm and about 2.23 mm. In a more particular embodiment, the height 17 of the body of the blade is about 2.18+/−0.25 mm.

Again referring to FIG. 1C, in a particular embodiment, the width 18 of the body of the blade is between about 0.3 mm and about 0.9 mm. In another embodiment, the width 18 of the body of the blade is between about 0.45 mm and about 0.75 mm. In a particular embodiment, the width 18 the body of the blade is about 0.64+/−0.25 mm.

Figure 2:
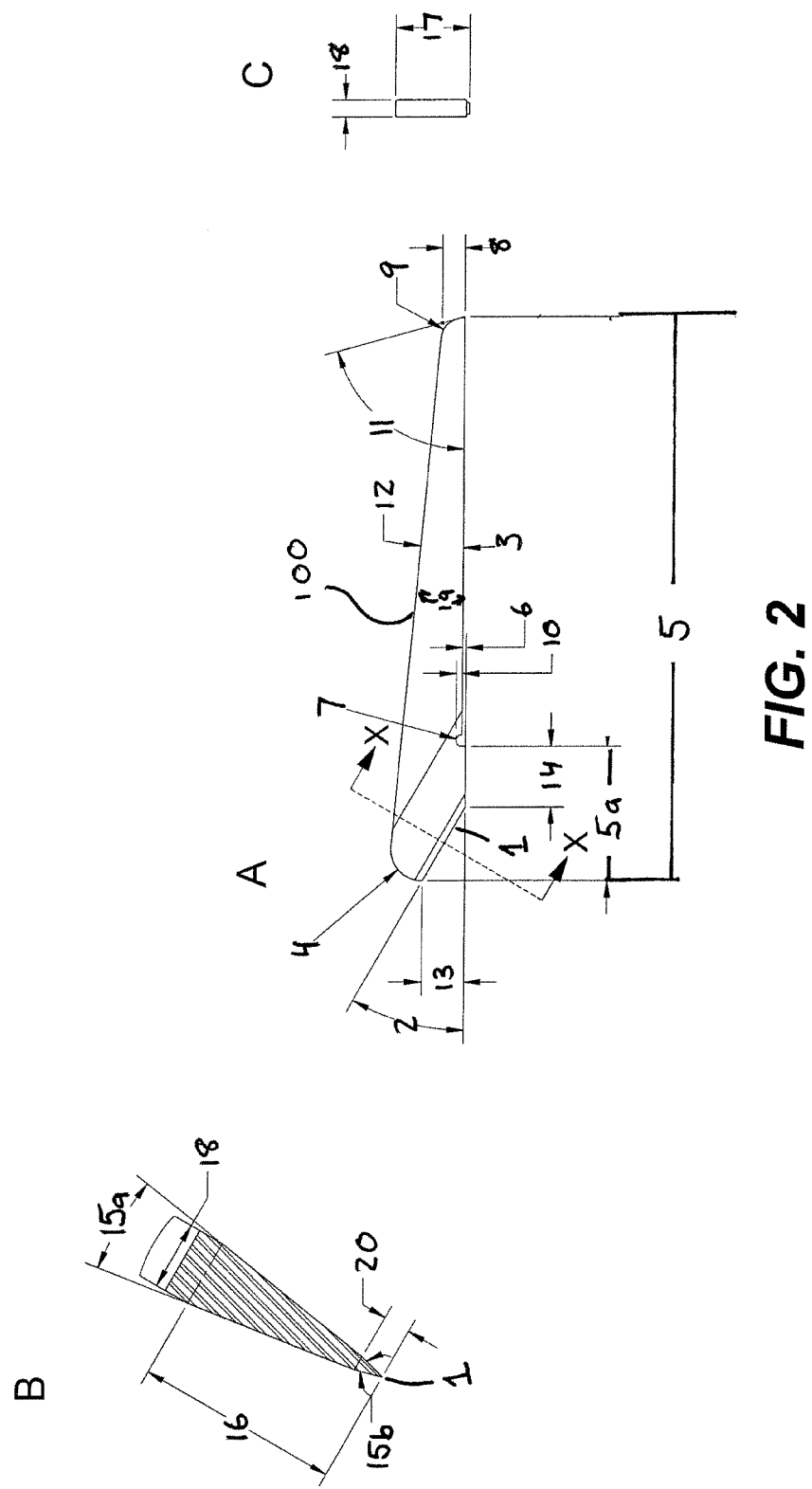
FIGS. 2A-C illustrate another embodiment of a blade component of an endoscopic knife assembly.
Figure 3:
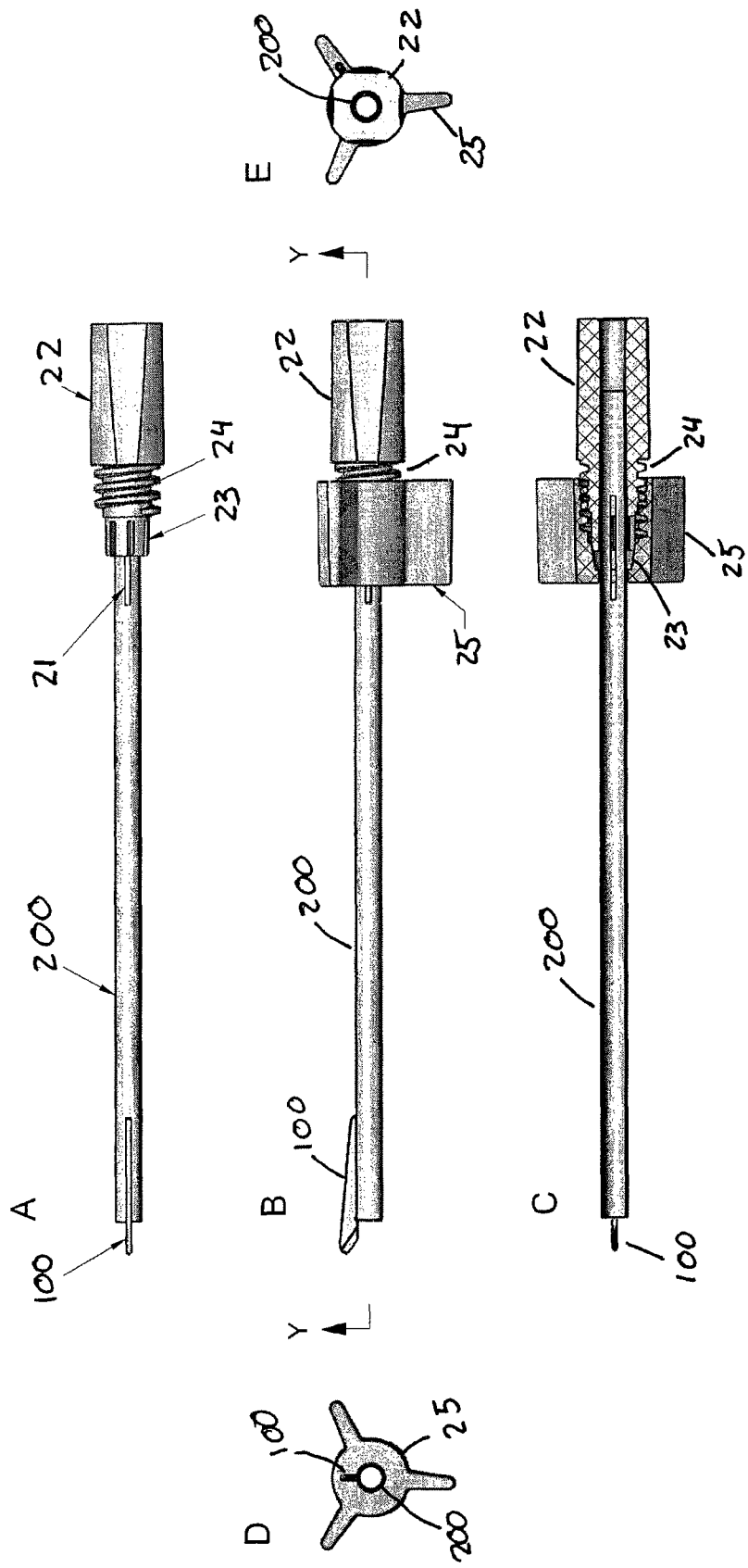
FIGS. 3A-E illustrate an endoscopic knife assembly for manual operation.
Figure 4:
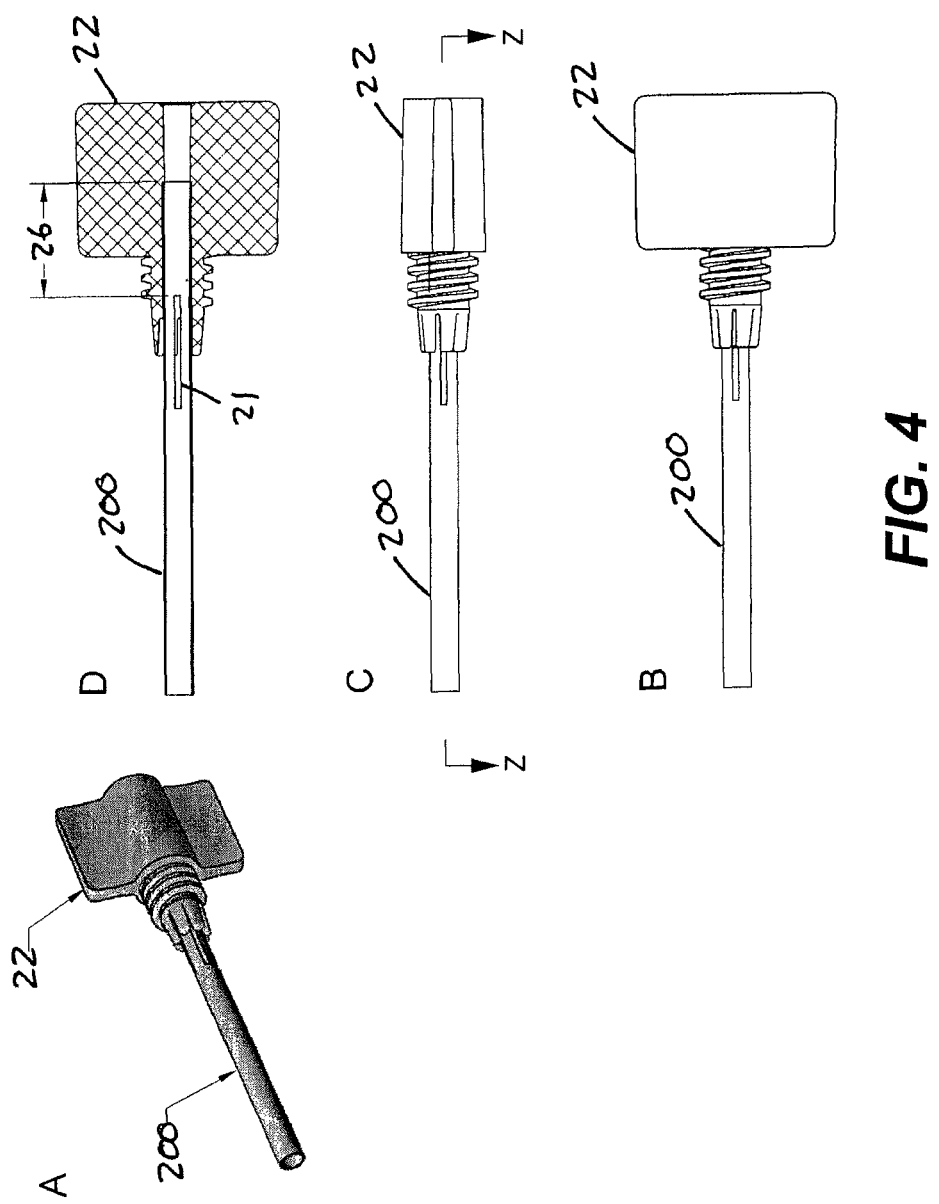
FIGS. 4A-D illustrate the a knife tube component of an endoscopic knife tube for manual operation.

FIG. 2A depicts a side view of another embodiment of the blade component of the endoscopic knife assembly, showing the cutting surface at the leading end of the blade, the transition where the blade is joined to the knife tube and the taper at the trailing end of the blade.

FIG. 2B is an view depicting an exemplary angle of the cutting surface of the blade as viewed from the perspective of the line X-X in FIG. 2A.

FIG. 2C is a perspective view of the blade in FIG. 2A from the back depicting the width of the blade and the transition between the mounting surface and the lower end of the cutting surface below the transition.

In a particular embodiment, the blade 100 as shown in FIG. 2A comprises a cutting surface 1 on the leading end of the blade, which is at an angle 2 with respect to the horizontal orientation of the blade 100, as defined by the mounting surface 3 of the blade. The angle 2 is such that the top of cutting surface 1 is forward of the bottom of the cutting surface. In one embodiment the angle 2 is between about 20 and about 40 degrees. In a particular embodiment, the angle 2 is between about 25 and about 35 degrees. In a more particular embodiment, the angle 2 is about 30 degrees.

In some embodiments, the upper end 4 of the cutting surface 1 is radiused. The radiused upper end 4 of the cutting surface 1 is about 90 degrees of a circle and has a radius measurement between about 0.50 mm and 1.50 mm. In a particular embodiment, the radius is about 0.94 mm.

In some embodiments, the cutting surface 1 has a vertical height 13 between about 0.80 mm and about 1.70 mm. In particular embodiments, the vertical height 13 is between about 1.00 mm and 1.50 mm. In a more particular embodiment, the vertical height 13 is about 1.27 mm.

In a particular embodiment, the total length 5 of the blade from the leading point of the cutting surface 1 to the trailing end of the blade is between about 13 mm and about 21 mm. In another particular embodiment, the total length 5 of the blade from the leading point of the cutting surface to the trailing end of the blade is between about 15 mm and about 19 mm. In a more particular embodiment the total length 5 of the blade is about 16.69+/−0.254 mm. In a particular embodiment, the length 5a of the forward section of the blade from the leading point of the cutting surface 1 to the leading edge of the notch 7 is between about 2 mm and about 8 mm. In another particular embodiment, the length 5a of the forward section of the blade from the leading point of the cutting surface to the leading edge of the notch 7 is between about 3 mm and about 5 mm. In a more particular embodiment the length 5a of the forward section of the blade is about 4+/−0.254 mm.

In order to insure that, during manufacture, the blade is consistently joined to the knife tube in the same location, the lower surface of the main body of the blade comprises a transition 6, the distal end of which meets the notch 7 in the lower surface of the main body of the blade. During assembly of the endoscopic knife assembly, the mounting surface 3 is aligned with and positioned on the forward end of the knife tube. Following the positioning of the blade on the knife tube, the blade is laser welded all around to the knife tube. In a particular embodiment, the strength of the weld is tested by applying torque to the unit, for example about 10 in-lbs of torque. In a first embodiment, the depth of the transition 6 is between about 0.03 mm and about 0.18 mm. In a particular embodiment, the depth of the transition 6 is between about 0.05 mm and about 0.15 mm. In a more particular embodiment, the depth of the transition 6 is about 0.10 mm.

In particular embodiments, the blade further comprises a notch 7 on the lower edge of the blade between the mounting surface 3 and the cutting surface 1. In particular embodiments, the notch 7 is relatively semi-circular in shape, having a radius of between about 0.1 mm and about 0.3 mm, more particularly about 0.18 mm. The top of the notch 7 is recessed 10 into the body of the blade, with respect to the bottom end of the cutting surface 1, between about 0.1 mm and about 0.3 mm, more particularly about 0.18 mm.

In particular embodiments, the horizontal distance 14 between the bottom of the leading edge of the cutting surface 1 and the notch 7 can be different, dependent upon the application for the blade. In some embodiments, the horizontal distance is between about 1.50 mm and about 2.50 mm. In further embodiments, the horizontal distance is between about 1.65 mm and about 2.0 mm. In a more particular embodiment, the horizontal distance 14 is about 1.80 mm.

In order to prevent the blade from catching on tissues or a cannula when the blade is drawn backwards through a cannula tube, the trailing edge 8 of the blade is angled down to the knife tube and the top of the trailing edge 8 is radiused 9. In a particular embodiment, the vertical height of the trailing edge 8 is between about 0.50 mm and about 0.88 mm, more particularly about 0.60 mm to about 0.70 mm. In a more particular embodiment, the vertical height of the trailing edge 8 is about 0.66 mm. In some embodiments, the radius 9 at the top of the trailing edge 8 is between about 0.40 mm and about 0.80 mm. In further embodiments, the radius 9 at the top of the trailing edge 8 is between about 0.50 mm and about 0.70 mm, more particularly about 0.61 mm.

In some embodiments the trailing edge 8 is canted forward at an angle 11 from the vertical with respect to the horizontal line of the mounting surface 3. in particular embodiments, the forward angle 11 of the trailing edge 8 is between about 30 degrees and about 90 degrees. In further embodiments, the angle 11 is between about 45 degrees and about 85 degrees. In more particular embodiments, the angle 11 is between about 65 degrees and about 80 degrees. In a most particular embodiment, the angle 11 is about 75 degrees.

In some embodiments, the top edge 12 of the blade 100 forms an angle 19 with respect to bottom edge 3, sloping downward as defined by FIG. 2A from where it meets the radius 4 at the top of cutting surface 1 to where it meets the radius 9 at the top of the trailing edge 8. In particular embodiments, the angle 19 of the top edge 12 is between about 2.5 degrees and about 10 degrees. In more particular embodiments, the angle 19 of the top edge 12 is between about 15 degrees and about 7 degrees. In a still more particular embodiment, the angle 19 of the top edge is about 5 degrees.

Referring now to FIG. 2B, in some embodiments, the cutting surface 1 is ground to form a double beveled surface over its depth 16. In particular embodiments, the cutting surface 1 has a depth 16 of between about 1.0 mm and about 2.0 mm. In further particular embodiments, the cutting surface 1 has a depth 16 of between about 1.25 mm and about 1.75 mm. In more particular embodiments, the cutting surface 1 has a depth 16 of about 1.5 mm. In particular embodiments, the double beveled cutting surface 1 is ground to comprise a first angle 15a over its depth 16 of between about 5 degrees and about 30 degrees. In further embodiments, the first angle 15a is between about 12 degrees and about 22 degrees. In a more particular embodiment, the first angle 15a is about 17 degrees.

In some embodiments, the double beveled cutting surface 1 is ground again over the depth of its leadingmost edge 20 to a second angle 15b. In particular embodiments, the leadingmost edge 20 of cutting surface 1 has a depth of between about 0.05 mm and about 0.4 mm. In further particular embodiments, the leadingmost edge 20 of cutting surface 1 has a depth of between about 0.1 mm and about 0.3 mm. In more particular embodiments, the leadingmost edge 20 of cutting surface 1 has a depth of about 0.2 mm.

In particular embodiments, the leadingmost edge 20 of double beveled cutting surface 1 is ground to comprise a second angle 15b over its depth of between about 20 degrees and about 45 degrees. In further embodiments, the second angle 15b is between about 25 degrees and about 36 degrees. In a more particular embodiment, the second angle 15b is about 31 degrees.

Referring to FIG. 2C, in a particular embodiment, the height 17 of the body of the blade is between about 1.8 mm and about 2.6 mm. In another embodiment, the height 17 of the body of the blade is between about 2.1 mm and about 2.3 mm. In a particular embodiment, the height 17 of the body of the blade is between about 2.15 mm and about 2.23 mm. In a more particular embodiment, the height 17 of the body of the blade is about 2.18+/−0.25 mm.

Again referring to FIG. 2C, in a particular embodiments, the width 18 of the body of the blade is between about 0.3 mm and about 0.9 mm. In another embodiment, the width 18 of the body of the blade is between about 0.45 mm and about 0.75 mm. In a more particular embodiment, the width 18 the body of the blade is about 0.5+/−0.25 mm. In a still more particular embodiment, the width 18 the body of the blade is about 0.51+/−0.03 mm.

The blade 100 is affixed onto a knife tube, such as, but not limited to, those exemplified in FIGS. 3-7.

In some embodiments, as exemplified in FIGS. 3A-E, the knife tube is part of a handheld endoscopic knife assembly, having at least a blade 100, a knife tube 200 and a handle. In some embodiments, the knife tube 200 comprises slits 21 in the tube for proper alignment of the tube in the handle 22, as shown in FIG. 3A. In particular embodiments, the knife tube 200 is held in the handle 22 by means of friction and/or pressure. For example, knife tube 200 is inserted into the handle 22. Handle 22 comprises compression fingers 23 for gripping the knife tube 200 and a threaded region 24 as shown in FIG. 3A for the attachment of a clamping nut 25 as shown in FIG. 3B. The clamping nut 25 is tightened on the threads 24 such that the knife tube 200 is contacted and securely held by the compression fingers 23 of the handle 22. FIG. 3C is a cross-section view of the handheld endoscopic knife assembly when viewed along the line Y-Y in FIG. 3B in the direction of the arrows. FIG. 3C shows the contacting of the compression fingers against the knife tube 200 as the compression nut 25 is tightened on the threads 24 of the handle 22.

FIG. 3D is an end view from the knife blade end of an exemplary endoscopic knife assembly showing the blade 100, knife tube 200 and compression nut 25. FIG. 3E is an end view from the handle end of an exemplary endoscopic knife assembly showing the handle 200, knife tube 200 and compression nut 25.

Referring now to FIGS. 3C-E in particular, in some embodiments, the knife tube 200 and handle 22 each comprise a hollow center lumen that allows the insertion of an endoscopic visualization device, such as an arthroscope. Insertion of a visualization device into the knife tube allows for the direct visualization of the knife blade and bodily tissues as the endoscopic knife assembly is being inserted into a cannula, as a cut is made of a tissue, such as separation of a tendon, and/or as the endoscopic knife assembly is being withdrawn.

While one particular embodiment of handle having four flattened surfaces for gripping the handle is depicted here, the physical design of the handle 22 is not intended to be limited to the embodiment as depicted in FIGS. 3A-C and E. Rather, the present application contemplates any design of handle 22 that serves the purpose of allowing a practitioner to grip the handle 22 for the use of the endoscopic knife assembly. Similarly, while one particular embodiment of compression nut having three gripping surfaces for turning the nut is depicted here, the physical design of compression nut 25 is not intended to be limited to the embodiment as depicted in FIGS. 3B-E. Rather, the present application contemplates any design of compression nut 25 that serves the purpose of holding the knife tube 200 in a handle for the use of the endoscopic knife assembly.

In some alternative embodiments, as exemplified in FIGS. 4A-D, the knife tube is part of a handheld endoscopic knife assembly, having at least a blade 100, a knife tube 200 and a handle, wherein the handle 22 has been affixed to the knife tube by adhesive means. As used herein, "adhesive means" refers to the bonding of the handle to the knife tube through the use of glue, epoxy, resin, solvents, laser or heat. For example, as depicted in FIG. 4D, which is a is a cross-section view of the handheld endoscopic knife assembly when viewed along the line Z-Z in FIG. 4C in the direction of the arrows, the area 26 between the slits 21 and the back end of the knife tube 200 provides a surface for the application of an epoxy.

While one particular embodiment of handle having two opposing protrusions for gripping the handle is depicted here, the physical design of the handle 22 is not intended to be limited to the embodiment as depicted in FIGS. 4A-D. Rather, the present application contemplates any design of handle 22 that serves the purpose of allowing a practitioner to grip the handle 22 for the use of the endoscopic knife assembly. Furthermore, the present application contemplates any design of handle 22 for attaching to the knife tube by adhesive means whether or not the handle comprises compression fingers or a threaded region.

In another aspect of the present application, the endoscopic knife assembly comprises a knife tube that is configured for locking attachment of the endoscopic knife assembly to an endoscope.

FIGS. 5A-D show an endoscopic assembly with a blade 100 mounted on a knife tube 200. As shown in FIG. 5A, the hook blade 100 is attached to the knife tube 200 having an alignment ring 250, such that the blade 100 is welded to the knife tube 200.

The knife tube 200 can optionally be marked on the top or side surface with gradations as exemplified in FIG. 5B to show the distance 41 to the distal end of the knife tube, or to a specific point on the leading edge of the cutting surface. As a non-limiting example, major gradations 42 can be made to show each centimeter in distance from the distal end of the knife tube, with minor gradations 43 between them to show each 1, 2, 2.5 or 5 millimeters. While the gradations can be applied to the knife tube by any means known in the art, it is preferable to lasermark the gradations on the knife tube 200 for accuracy and permanence. Additionally, the knife tube 200 can also be marked in a similar manner with additional information, for example on the bottom or a side surface of the knife tube 200. Exemplary markings may include, but are not limited to, a maker's mark, part number, lot number and an indication that the endoscopic knife assembly is intended for only a single use.

Referring to FIG. 5A-C, showing side, top and bottom views of the endoscopic knife assembly, an alignment ring 250 is affixed near the proximate end of the knife tube 200. In one embodiment, the alignment ring 250 is affixed in position on the knife tube 200 using USP Class VI gamma irradiation and steam resistant epoxy adhesive during assembly. In some embodiments, a two part epoxy such as MASTERBOND EP42 HT™ or ARMSTRONG C-7™, or a suitable equivalent thereof is used. In one embodiment, the distance 44 between the alignment ring 250 and the proximate end of the knife tube 200 is between about 15 mm and about 25 mm. In another embodiment, the distance 44 is between about 18.67 mm and about 19.43 mm. In another embodiment, the distance 44 is about 19.05+/−0.38 mm.

As shown in FIGS. 5A-D, in particular embodiments, the alignment ring 250 comprises a flattened surface 252 that is aligned on the opposite side of the knife tube 200 as the blade 100. the plane of the flattened surface 252 of the alignment ring 250 is oriented perpendicular to the plane in which the blade is affixed to the knife tube 200.

The knife tube further comprises slots 45 in the proximate end that are positioned on the sides of the knife tube 200, perpendicular to the blade mounted on the top of the knife tube. The slots 45 in particular embodiments extend forward to where the alignment ring 250 is affixed to the knife tube 200. In some applications, the slots 45 may not extend forward to where the alignment ring 250 is affixed to the knife tube 200. In one embodiment, the slots 45 have a width of between about 0.4 mm and about 1.1 mm wide, more particularly between about 0.53 mm and about 0.91 mm wide. Even more particularly, the width of the slots 45 is about 0.66 mm.

The slots and alignment ring provide an attachment point for a locking device, in order to mount an endoscope to the scope-mounting blade or endoscopic knife assembly.

Referring to FIGS. 5A-C, in some embodiments, the knife tube 200 has a flared proximate end 46. In one embodiment, about 0.2 to about 0.5 most proximate millimeters of the knife tube 200 are flared. In another embodiment, about the 0.38 most proximate millimeters of the knife tube 200 are flared. In another embodiment, the flared proximate end 46 has a flare angle of about 20 to 40 degrees, more particularly about 30 degrees. In still another embodiment, the outer diameter of the flared proximate end 46 of the knife tube is about 0.25 mm to about 0.45 mm, more particularly about 0.36 mm to about 0.37 mm.

Referring now to FIG. 5D, the inner diameter of the knife tube 200 is such that an endoscope or arthroscope camera can be inserted into the knife tube in order to show the blade and the target tissue during a procedure. In one embodiment, the inner diameter is between about 2 mm and about 3.5 mm. In a particular embodiment, the inner diameter is between about 2.6 mm and about 3.0 mm. In a more particular embodiment, the inner diameter is about 2.8 mm.

FIGS. 6A-D show an alternative embodiment of an endoscopic assembly with a blade 100 mounted on a knife tube 200. As shown in FIG. 6A, the hook blade 100 is attached to the knife tube 200 having an alignment ring 250, such that the blade 100 is welded to the knife tube 200.

The knife tube 200 can optionally be marked on the top or side surface with gradations as exemplified in FIG. 6B to show the distance 41 to the distal end of the knife tube, or to a specific point on the leading edge of the cutting surface. As a non-limiting example, major gradations 42 can be made to show each centimeter in distance from the distal end of the knife tube, with minor gradations 43 between them to show each 1, 2, 2.5 or 5 millimeters. While the gradations can be applied to the knife tube by any means known in the art, it is preferable to lasermark the gradations on the knife tube 200 for accuracy and permanence. Additionally, the knife tube 200 can also be marked in a similar manner with additional information, for example on the bottom or a side surface of the knife tube 200. Exemplary markings may include, but are not limited to, a maker's mark, part number, lot number and an indication that the endoscopic knife assembly is intended for only a single use.

Referring to FIG. 6A-C, showing side, top and bottom views of the endoscopic knife assembly, an alignment ring 250 is affixed near the proximate end of the knife tube 200. In one embodiment, the alignment ring 250 is affixed in position on the knife tube 200 using USP Class VI gamma irradiation and steam resistant epoxy adhesive during assembly. In some embodiments, a two part epoxy such as MASTERBOND EP42 HT™ or ARMSTRONG C-7™, or a suitable equivalent thereof is used. In one embodiment, the distance 44 between the alignment ring 250 and the proximate end of the knife tube 200 is between about 15 mm and about 25 mm. In another embodiment, the distance 44 is between about 18.67 mm and about 19.43 mm. In another embodiment, the distance 44 is about 19.05+/−0.38 mm.

As shown in FIGS. 6A-D, in particular embodiments, the alignment ring 250 comprises a flattened surface 252 that is aligned on the same side of the knife tube 200 as the blade 100. the plane of the flattened surface 252 of the alignment ring 250 is oriented perpendicular to the plane in which the blade is affixed to the knife tube 200.

The knife tube further comprises slots 45 in the proximate end that are positioned on the sides of the knife tube 200, perpendicular to the blade mounted on the top of the knife tube. The slots 45 in particular embodiments extend forward to where the alignment ring 250 is affixed to the knife tube 200. In some applications, the slots 45 may not extend forward to where the alignment ring 250 is affixed to the knife tube 200. In one embodiment, the slots 45 have a width of between about 0.4 mm and about 1.1 mm wide, more particularly between about 0.53 mm and about 0.91 mm wide. Even more particularly, the width of the slots 45 is about 0.66 mm.

The slots and alignment ring provide an attachment point for a locking device, in order to mount an endoscope to the scope-mounting blade or endoscopic knife assembly.

Referring to FIGS. 6A-C, in some embodiments, the knife tube 200 has a flared proximate end 46. In one embodiment, about 0.2 to about 0.5 most proximate millimeters of the knife tube 200 are flared. In another embodiment, about the 0.38 most proximate millimeters of the knife tube 200 are flared. In a particular embodiment, the angle of the flare is between about 40 and 80 degrees, more particularly between about 50 and 70 degrees, and still more particularly about 60 degrees. In still another embodiment, the outer diameter of the flared proximate end 46 of the knife tube is about 0.25 mm to about 0.45 mm, more particularly about 0.36 mm to about 0.37 mm.

Referring now to FIG. 6D, the inner diameter of the knife tube 200 is such that an endoscope or arthroscope camera can be inserted into the knife tube in order to show the blade and the target tissue during a procedure. In one embodiment, the inner diameter is between about 2 mm and about 3.5 mm. In a particular embodiment, the inner diameter is between about 2.6 mm and about 3.0 mm. In a more particular embodiment, the inner diameter is about 2.8 mm.

FIGS. 7A-C are perspective views of a knife tube 200 without an affixed blade or alignment ring and without gradations.

FIG. 7A is a perspective view from the side of a knife tube 200. In a particular embodiment, the outer diameter 51 of the knife tube 200 is between about 2.8 mm and about 3.6 mm, preferably between about 3.073 mm and about 3.175 mm. In a more preferred embodiment, the outer diameter 144 is about 3.14+/−0.03 mm. In a still more preferred embodiment, the outer diameter 144 is about 3.14+/−0.01 mm.

In another particular embodiment, the posterior end of the knife tube 200 is flared 46 In particular, the about 0.2 to about 0.6 most posterior millimeters of the knife tube 200 are flared. In a more particular embodiment, the about 0.38 or about 0.38 to about 0.54 most posterior millimeters of the knife tube 200 are flared. In a still more particular embodiment, about the 0.46 most posterior millimeters of the knife tube 200 are flared. In a particular embodiment, the angle 53 of the flare is between about 40 and 80 degrees, more particularly between about 50 and 70 degrees, and still more particularly about 60 degrees. In still another preferred embodiment, the outer diameter 54 of the flared portion 46 of the knife tube 200 is between about 0.25 mm and about 0.45 mm, more particularly between about 0.3 mm and about 0.4 mm, and still more particularly about 0.358 mm.

FIG. 7B is a perspective view from the top or bottom of a knife tube. In a particular embodiment, the length 52 of the knife tube 200 is between about 20 mm and about 100 mm. In a further particular embodiment, the length 52 of the knife tube 200 is between about 30 mm and about 80 mm. In a still further particular embodiment, the length 52 of the knife tube 200 is between about 40 mm and about 70 mm. In a yet further particular embodiment, the length 52 of the knife tube 200 is between about 50 mm and about 60 mm. In a more particular embodiment, the length 52 of the knife tube 200 is about 55 mm.

FIG. 7C is a perspective view of the posterior end of a knife tube 200, showing the slots 45 and the flared end. In particular embodiments, the slots 45 are between about 0.4 mm and about 1.1 mm wide, more particularly between about 0.53 mm and about 0.91 mm wide. Even more particularly, the width 148 of the slots is about 0.66 mm.

Figure 8:
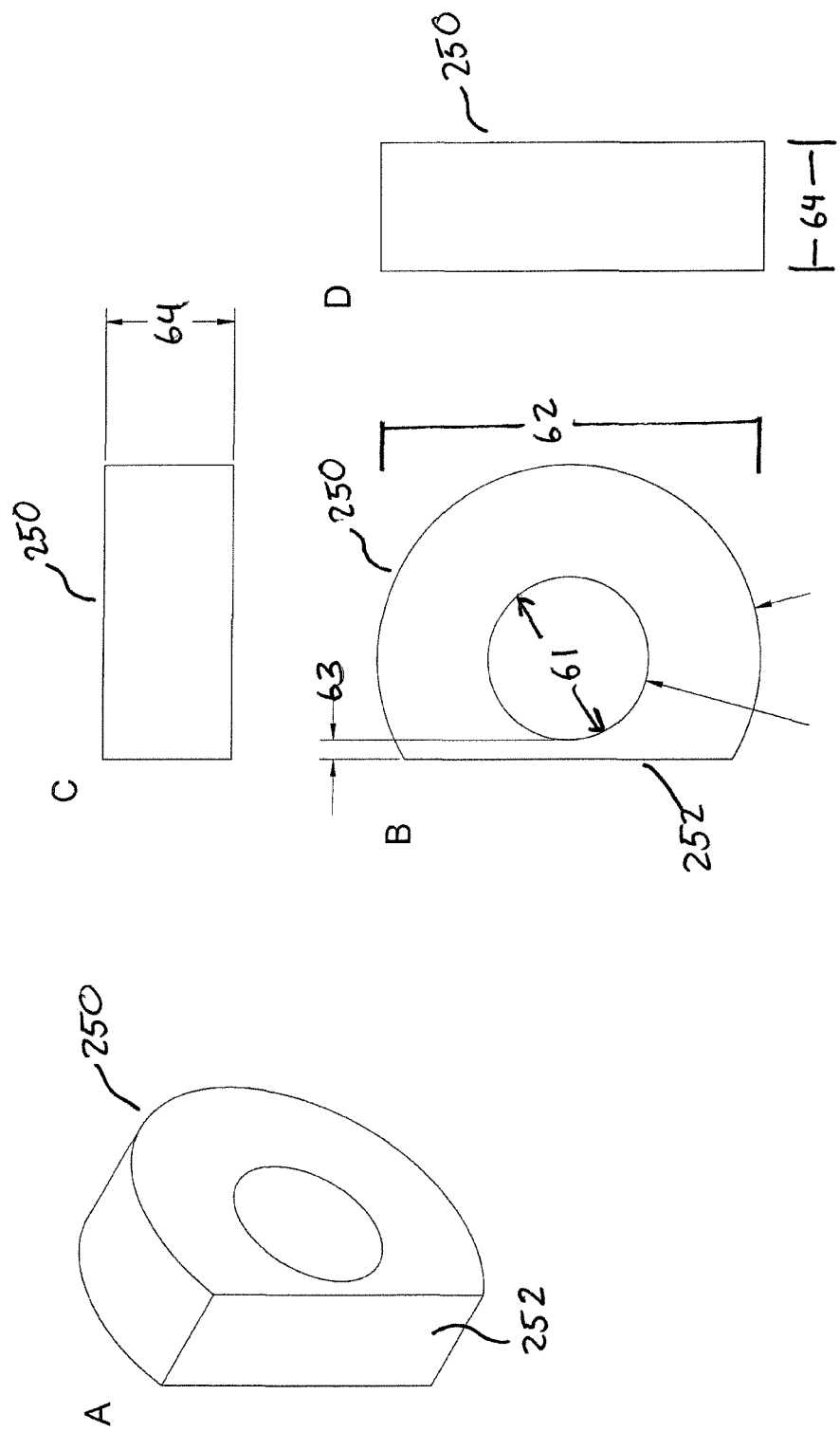
FIGS. 8A-D illustrate the alignment ring component of the endoscopic knife assembly of FIGS. 5A-D and 6A-D.

FIGS. 8A-D show an embodiment of the alignment ring 250 of the endoscopic knife assembly of the application. Referring now to FIG. 8A, in one embodiment, the alignment ring 250 has a flattened surface 252 that, when the alignment ring 250 is affixed to the knife tube 200, is oriented on the bottom of the knife tube 200, i.e., opposite of the mounting of the blade 100, as also shown in FIG. 5D; or is oriented on the top of the knife tube 200, i.e., on the same side of the mounting of the blade 100, as also shown in FIG. 6D. When the endoscopic knife assembly is fully assembled, the flattened surface 252 of the alignment ring forms a right angle with the vertical orientation of the affixed blade 100.

In one embodiment, the inner diameter 61 of the alignment ring, which must fit on the outside of the knife tube 200, is between about 2.6 mm and about 3.7 mm, particularly between about 3.0 mm and about 3.4 mm. In a more particular embodiment, the inner diameter 61 is about 3.2+/−0.2 mm. In a still more particular embodiment, the inner diameter 51 is about 3.2+/−0.05 mm.

In a particular embodiment, the outer diameter 62 of the alignment ring is between about 6 mm and about 10 mm, more particularly between about 7.3 mm and about 7.9 mm. In a still more particular embodiment, the outer diameter 62 is about 7.62+/−0.2 mm. In a still more particular embodiment, the outer diameter 62 is about 7.62+/−0.05 mm.

As shown in FIG. 8B, in one embodiment, the distance 63 between the inner opening of the alignment ring and the flattened surface 252, on a line perpendicular to the flattened surface 252, is between about 0.25 mm and about 0.5 mm, more particularly between about 0.30 mm and about 0.45 mm. In a still more particular embodiment, the distance 63 is about 0.38 mm.

Referring to FIG. 8C, showing a side view of the alignment ring, and FIG. 8D, showing a view from the top of the alignment ring, in one embodiment, the alignment ring 250 has a thickness 64 of between about 1.0 mm and about 4.0 mm. In a particular embodiment, the thickness 64 is between about 2.0 mm and about 3.0 mm. In a more particular embodiment, the thickness 64 is about 2.54 mm.

Instrument Kit

Another aspect of the present application relates to an instrument kit for implementing an endoscopic surgical procedure. The instrument kit contains an endoscopic knife assembly having a low-profile downward-angled blade, a cannula guide member comprising a longitudinal bore having open proximal and distal ends and an open slot extending along the length thereof communicating with the open ends, and an elongate insertion member that is slidably receivable within the cannula guide member and is configured so that at least portions thereof conform with the open distal end and the open slot of the guide member to form a smooth exterior surface in combination therewith.

In one embodiment, the instrument kit further includes an endoscope sized for insertion into the cannula guide member for direct visualization of an operative site.

In another embodiment, the endoscope is capable to carry a cutting instrument at a leading end. The endoscope is insertable into the cannula guide member such that the cutting instrument protrudes through the open slot in the cannula guide member.

In another embodiment, the instrument kit further includes an elevator.

In another embodiment, the instrument kit further includes a depth gauge mountable to a leading end of the endoscope.

In another embodiment, the instrument kit further includes a locking device capable of locking the endoscope and the cannula guide member into mutually fixed positions.

In another embodiment, the instrument kit further includes a stop device mountable on the cannula guide member to prevent excessive penetration at a surgical site by the cutting instrument. In another embodiment, the instrument kit further includes a curved dissector.

Methods

Another aspect of the present application relates to a method for uniportal endoscopic surgery. Uniportal endoscopic surgery allows the practitioner to visualize a target tissue and its surrounding tissues as well as perform a surgical procedure through a single entry portal. In some instances, the entry portal may be a natural opening, while in other instances the entry portal is an incision. In the case of an incision, generally only a single small incision must be made. In particular embodiments, the incision is less than or equal to about 2 cm in length. In more particular embodiments, the incision is less than or equal to about 1.5 cm in length. In still more particular embodiments, the incision is less than or equal to about 1 cm in length. The single small incision allows the patient to recover more quickly and begin therapy and/or resume normal activity as tolerated sooner.

The uniportal endoscopic surgical procedure described herein can be used to implement a number of different surgical procedures. In some embodiments, the uniportal endoscopic surgical procedure is selected from the group consisting of trigger finger release, carpal tunnel release, cubital tunnel release, plantar fascia release, lateral release for patella realignment, release of the extensor tendons, release of the posterior and other compartments of the leg, and forearm fascial release.

One aspect of the present application relates to a method for a performing a uniportal endoscopic surgical procedure on a target tissue in a subject. Generally, following the establishment of an entry portal, in some embodiments a blunt instrument, such as an elevator is inserted through the portal to establish an opening in the underlying tissue between the portal and the target tissue.

A cannula having open proximal and distal ends and an open slot extending along the length of the cannula is inserted into the entry portal and extended through to the target tissue. In particular embodiments, the cannula is made of a clear plastic material so that the entirety of the surrounding tissue can be viewed with an arthroscope. In order to facilitate insertion of the cannula, the central lumen of the cannula comprises an obturator, which is withdrawn following insertion of the cannula.

An arthroscope is inserted into the cannula to view the target tissue and the surrounding tissues, assuring that the slot of the cannula is in proper orientation to the target tissue. The arthroscope is withdrawn and an arthroscope with a mounted endoscopic knife assembly having a low-profile blade that has a downward angled cutting surface that is radiused at its upper end is advanced into the cannula, with the knife blade aligned with the slot of the cannula. In some embodiments, the arthroscope used for viewing the target tissue and the surrounding tissues is the same unit as the arthroscope comprising a mounted endoscopic knife assembly. In other embodiments, the arthroscope used for viewing the target tissue and the surrounding tissues is a different unit from the arthroscope comprising a mounted endoscopic knife assembly.

The arthroscope comprising a mounted endoscopic knife assembly is advanced further through the cannula so that the blade moves in contact with the target tissue through the slot, operatively engaging the target tissue with the blade. The blade is further advanced through the cannula to divide the target tissue.

In one particular embodiment, the operative procedure is trigger finger release.

In another particular embodiment, the establishing an entry portal comprises making an incision.

In another particular embodiment, the target tissue is the A1 pulley.

In another particular embodiment, the inserting of said arthroscope comprising an endoscopic knife assembly having a low-profile blade that has a downward angled cutting surface that is radiused at its upper end is followed by the insertion of an arthroscope comprising a means for visualization of the results of the endoscopic surgical procedure on the target tissue.

The present invention is further illustrated by the following examples which should not be construed as limiting. The contents of all references, patents and published patent applications cited throughout this application, as well as the Figures and Tables, are incorporated herein by reference.

EXAMPLE 1

Uniportal Endoscopic Trigger Release

In a patient presenting with trigger finger of the middle or ring finger, a 1 cm incision is made just proximal to the A1 pulley on the distal palmar crease proximate to the affected digit.

An elevator is introduced into the incision and used to create a plane superficial to the flexor tendon sheath. The elevator is withdrawn.

A slotted cannula with an obturator inserted therein is introduced into the incision and advanced through the plane created by the elevator. The slot of the cannula is oriented facing the flexor tendon sheath. The obturator is removed from the cannula.

Figure 9:
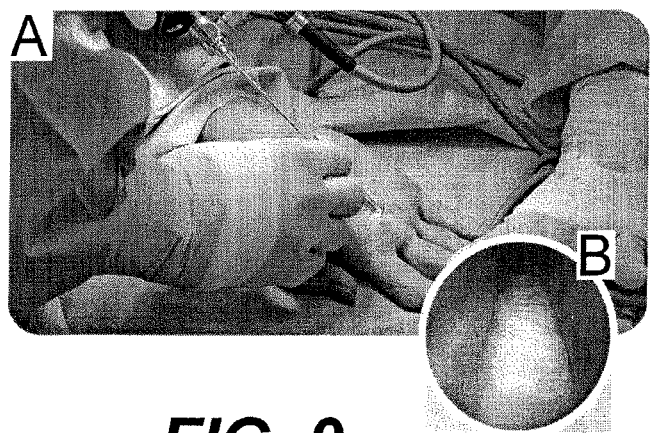
FIGS. 9A-B depict the visualization of the A1 and A2 pulleys in a uniportal endoscopic trigger finger release surgical procedure.

An arthroscope is introduced into the cannula and advanced to visualize the A1 pulley and A2 pulley as shown in FIGS. 9A-B. The arthroscope is withdrawn.

An endoscopic knife assembly having a low-profile downward-angled blade is fastened onto an arthroscope.

Figure 10:
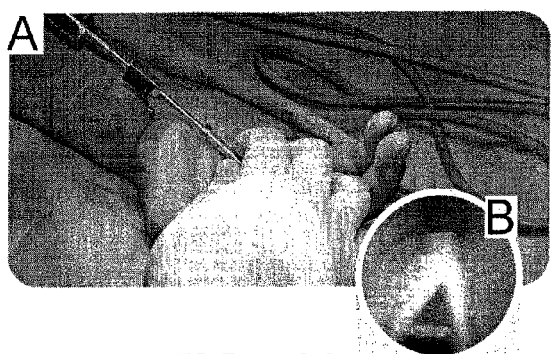
FIGS. 10A-B depict the direct viewing of the division of the A1 pulley during a uniportal endoscopic trigger finger release surgical procedure.

The scope and blade assembly is advanced into the cannula, dividing the A1 pulley. Having the endoscopic knife assembly mounted directly on the arthroscope allows direct visualization of the procedure from the point-of-view of the blade, allowing visualization of the A2 pulley and avoiding damage to the A2 pulley (FIGS. 10A-B). The scope and blade assembly is withdrawn from the cannula.

Figure 11:
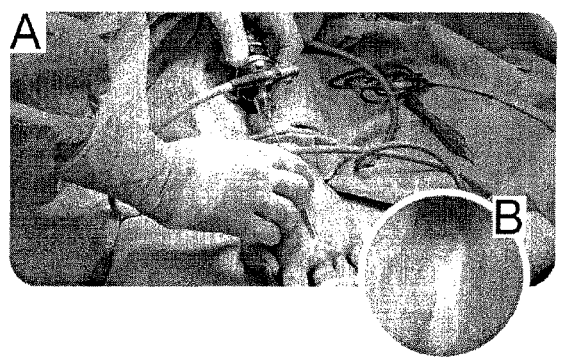
FIGS. 11A-B depict the visualization of the cut ends of the A1 pulley and of the underlying flexor tendon during a uniportal endoscopic trigger finger release surgical procedure.

An arthroscope is again advanced into the cannula to visualize the cut edges of the A1 pulley, as well as visualization of the underlying flexor tendon (FIGS. 11A-B).

While visualizing the tendon, release of the tendon is confirmed by passive manipulation of the digit through its range of motion.

The absence of triggering is confirmed by having the subject flex and extend the affected digit.

The arthroscope is withdrawn and the cannula is removed from the incision.

The wound is closed and a soft bandage is applied.

The patient is encouraged to begin early finger motion following surgery and to resume daily activities as tolerated.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the components and steps in any sequence which is effective to meet the objectives there intended, unless the context specifically indicates the contrary.

What is claimed is:

1. A method for treating trigger finger, comprising:
    establishing an entry portal at a location proximal to A1 pulley;
    inserting a cannula having open proximal and distal ends and an open slot extending along the length of the cannula;
    inserting an endoscope into the cannula, said endoscope comprising an endoscopic knife assembly comprising a low-profile blade that comprises a downward angled cutting surface, and a radiused surface at an upper end of the cutting surface,
    said endoscopic knife assembly further comprising a knife tube having a distal end and a proximate end, said low-profile blade further comprising a notch to engage with the knife tube, said knife tube an alignment ring attached near the proximate end and one or more slots at the proximate end for the attachment of a locking assembly to said knife tube and alignment ring, said alignment ring comprising a flattened surface that is positioned perpendicular to the low-profile blade attached to the distal end of the knife tube, wherein the flattened surface is located along the outer circumference of the alignment ring;
    advancing said endoscope so that the blade moves in contact with the A1 pulley through the slot;
    operatively engaging the A1 pulley with the blade; and
    advancing the blade through the cannula to divide the A1 pulley.

2. The method of claim 1, wherein the step of inserting an endoscope comprising an endoscopic knife assembly is preceded by the insertion of another endoscope to visualize anatomic structures surrounding the cannula.

3. The method of claim 1, wherein the cannula is made of a clear plastic material.

4. The method of claim 1, wherein the downward angled cutting surface has a downward angle of between about 20 degrees and about 40 degrees.

5. The method of claim 1, wherein the downward angled cutting surface is a double beveled cutting surface.

6. The method of claim 1, wherein the low-profile blade has a total vertical height in the range of about 1.8 mm to about 2.6 mm.

7. The method of claim 1, wherein the endoscopic knife assembly further comprises a handle at the proximal end of the knife tube.

8. The method of claim 1, wherein the one or more slots are located on a plane that is perpendicular to the blade attached to the distal end of the knife tube.

9. A method for performing a uniportal endoscopic surgical procedure in a subject, comprising:
    establishing an entry portal for a target tissue;
    inserting a cannula into the entry portal and advancing the cannula to the target tissue, wherein the cannula comprises an open proximal end, an open distal end, and an open slot extending along the length of the cannula;
    inserting an endoscope into the cannula, the endoscope comprising an endoscopic knife assembly comprising a low-profile blade that comprises a downward angled cutting surface and a non-cutting radiused surface at a top end of the cutting surfaces,
    said endoscopic knife assembly further comprising a knife tube having a distal end and a proximate end, said low-profile blade further comprising a notch to engage with the knife tube, said knife tube comprising an alignment ring attached near the proximate end and one or more slots at the proximate end for the attachment of a locking assembly to said knife tube and alignment ring, said alignment ring comprising a flattened surface that is positioned perpendicular to the low-profile blade attached to the distal end of the knife tube, wherein the flattened surface is located along the outer circumference of the alignment ring;

advancing the endoscope so that the blade moves in contact with the target tissue through the slot;

operatively engaging the target tissue with the blade; and advancing the blade through the cannula to divide the target tissue.

10. The method of claim 9, wherein the uniportal endoscopic surgical procedure is selected from the group consisting of carpal tunnel release, cubital tunnel release, plantar fascia release, lateral release for patella realignment, release of the extensor tendons, release of the posterior and other compartments of the leg, and forearm fascial release.

11. The method of claim 9, wherein the step of inserting an endoscope comprising an endoscopic knife assembly is preceded by the insertion of another endoscope to visualize anatomic structures surrounding the cannula.

12. The method of claim 9, wherein the cannula is made of a clear plastic material.

13. The method of claim 9, wherein the downward angled cutting surface has a downward angle of between about 20 degrees and about 40 degrees.

14. The method of claim 9, wherein the downward angled cutting surface is a double beveled cutting surface.

15. The method of claim 9, wherein the endoscopic knife assembly further comprises a knife tube having a distal end and a proximate end, and wherein the low-profile blade further comprises a notch to engage with the knife tube.

16. The method of claim 15, wherein the knife tube comprises an alignment ring attached near the proximate end and one or more slots at the proximate end for the attachment of a locking assembly to the knife tube and alignment ring.

* * * * *